(12) United States Patent
Zhu

(10) Patent No.: US 11,938,323 B2
(45) Date of Patent: Mar. 26, 2024

(54) NEURAL STIMULATION WITH DECOMPOSITION OF EVOKED COMPOUND ACTION POTENTIALS

(71) Applicant: Boston Scientific Neuromodulation Corporation, Valencia, CA (US)

(72) Inventor: Changfang Zhu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 267 days.

(21) Appl. No.: 17/449,202

(22) Filed: Sep. 28, 2021

(65) Prior Publication Data

US 2022/0008729 A1 Jan. 13, 2022

Related U.S. Application Data

(63) Continuation of application No. 16/291,923, filed on Mar. 4, 2019, now abandoned.

(60) Provisional application No. 62/641,748, filed on Mar. 12, 2018.

(51) Int. Cl.
*A61N 1/36* (2006.01)
*A61B 5/24* (2021.01)
*A61N 1/372* (2006.01)

(52) U.S. Cl.
CPC ............ *A61N 1/36139* (2013.01); *A61B 5/24* (2021.01); *A61N 1/36062* (2017.08); *A61N 1/36128* (2013.01); *A61N 1/36132* (2013.01); *A61N 1/36153* (2013.01); *A61N 1/36171* (2013.01); *A61N 1/36175* (2013.01); *A61N 1/36192* (2013.01); *A61N 1/37235* (2013.01)

(58) Field of Classification Search
None
See application file for complete search history.

(56) References Cited

U.S. PATENT DOCUMENTS

| 5,697,958 | A | 12/1997 | Paul et al. |
| 5,702,429 | A | 12/1997 | King |
| 5,902,236 | A | 5/1999 | Iversen |
| 5,902,249 | A | 5/1999 | Lyster |
| 5,913,882 | A | 6/1999 | King |

(Continued)

FOREIGN PATENT DOCUMENTS

| WO | 2015/077362 | 5/2015 |
| WO | 2017/100866 | 6/2017 |

(Continued)

OTHER PUBLICATIONS

Akhoun, Idrick, et al., "Electrically Evoked Compound Action Potential Artifact Rejection by Independent Component Analysis: Technique Validation," Hearing Research, Aug. 2013, 302, 60-73.

(Continued)

*Primary Examiner* — Carl H Layno
*Assistant Examiner* — Manolis Pahakis
(74) *Attorney, Agent, or Firm* — Lewis & Reese, PLLC

(57) ABSTRACT

Methods and systems for providing neuromodulation to a patient are disclosed. The disclosed methods and systems use sensed neural responses to construct and optimize models of the neural elements recruited during the neuromodulation. The models are used to estimate neural recruitment associated with a therapeutic effect and/or with side-effects to stimulation. The models can be used to adjust neuromodulation in a closed-loop fashion.

15 Claims, 10 Drawing Sheets

(56) References Cited

U.S. PATENT DOCUMENTS

| | | |
|---|---|---|
| 6,181,969 B1 | 1/2001 | Gord et al. |
| 6,516,227 B1 | 2/2003 | Meadows et al. |
| 7,024,247 B2 | 4/2006 | Gliner et al. |
| 7,424,322 B2 | 9/2008 | Lombardi et al. |
| 7,450,992 B1 | 11/2008 | Cameron |
| 8,233,992 B2 | 7/2012 | Zhu et al. |
| 8,255,057 B2 | 8/2012 | Fang et al. |
| 8,335,664 B2 | 12/2012 | Eberle |
| 8,352,030 B2 | 1/2013 | Denison |
| 8,606,362 B2 | 12/2013 | He et al. |
| 8,620,436 B2 | 12/2013 | Parramon et al. |
| 8,768,453 B2 | 7/2014 | Parramon et al. |
| 9,044,155 B2 | 6/2015 | Strahl |
| 9,061,140 B2 | 6/2015 | Shi et al. |
| 9,119,964 B2 | 9/2015 | Marnfeldt |
| 9,155,892 B2 | 10/2015 | Parker et al. |
| 9,248,274 B2 | 2/2016 | Troosters et al. |
| 9,248,279 B2 | 2/2016 | Chen et al. |
| 9,265,431 B2 | 2/2016 | Hincapie Ordonez et al. |
| 9,302,112 B2 | 4/2016 | Bornzin et al. |
| 9,381,356 B2 | 7/2016 | Parker et al. |
| 9,386,934 B2 | 7/2016 | Parker et al. |
| 9,387,325 B1 | 7/2016 | Min et al. |
| 9,403,013 B2 | 8/2016 | Walker et al. |
| 9,409,020 B2 | 8/2016 | Parker |
| 9,526,897 B2 | 12/2016 | Chen et al. |
| 9,533,148 B2 | 1/2017 | Carcieri et al. |
| 9,731,116 B2 | 8/2017 | Chen |
| 9,872,990 B2 | 1/2018 | Parker et al. |
| 9,974,455 B2 | 5/2018 | Parker et al. |
| 10,076,667 B2 | 9/2018 | Kaula et al. |
| 10,842,989 B2 | 11/2020 | Brill et al. |
| 11,172,864 B2* | 11/2021 | Parker ............... A61N 1/36067 |
| 2002/0156513 A1 | 10/2002 | Borkan |
| 2005/0246004 A1 | 11/2005 | Cameron et al. |
| 2008/0146894 A1 | 6/2008 | Bulkes et al. |
| 2008/0300655 A1 | 12/2008 | Cholette |
| 2012/0092031 A1 | 4/2012 | Shi et al. |
| 2012/0095519 A1 | 4/2012 | Parramon et al. |
| 2012/0095529 A1 | 4/2012 | Parramon et al. |
| 2012/0116741 A1* | 5/2012 | Choi .................... A61N 1/3614 703/11 |
| 2013/0289665 A1 | 10/2013 | Marnfeldt et al. |
| 2014/0066803 A1* | 3/2014 | Choi ..................... A61B 5/388 600/554 |
| 2014/0194772 A1 | 7/2014 | Single et al. |
| 2014/0236042 A1 | 8/2014 | Parker et al. |
| 2014/0236257 A1 | 8/2014 | Parker et al. |
| 2014/0243926 A1 | 8/2014 | Carcieri |
| 2014/0277452 A1 | 9/2014 | Jaax |
| 2014/0288551 A1 | 9/2014 | Bharmi et al. |
| 2014/0296737 A1 | 10/2014 | Parker et al. |
| 2014/0350634 A1 | 11/2014 | Grill et al. |
| 2015/0032181 A1 | 1/2015 | Baynham et al. |
| 2015/0360038 A1 | 5/2015 | Zottola et al. |
| 2015/0157861 A1 | 6/2015 | Aghassian et al. |
| 2015/0258337 A1 | 9/2015 | Long et al. |
| 2015/0282725 A1 | 10/2015 | Single et al. |
| 2015/0313487 A1 | 11/2015 | Single et al. |
| 2015/0360031 A1 | 12/2015 | Bornzin et al. |
| 2016/0157769 A1* | 6/2016 | Min ..................... A61B 5/4887 600/547 |
| 2016/0158550 A1 | 6/2016 | Hou et al. |
| 2016/0166164 A1 | 6/2016 | Obradovic et al. |
| 2016/0175594 A1 | 6/2016 | Min et al. |
| 2016/0287126 A1 | 10/2016 | Parker et al. |
| 2016/0287182 A1 | 10/2016 | Single et al. |
| 2017/0049345 A1 | 2/2017 | Single et al. |
| 2017/0071490 A1 | 3/2017 | Parker et al. |
| 2017/0135624 A1 | 5/2017 | Parker et al. |
| 2017/0173335 A1* | 6/2017 | Min .................. A61N 1/36178 |
| 2017/0216587 A1 | 8/2017 | Parker et al. |
| 2017/0296823 A1 | 10/2017 | Hershey et al. |
| 2017/0361101 A1 | 12/2017 | Single et al. |
| 2018/0071520 A1 | 3/2018 | Weerakoon et al. |
| 2018/0071527 A1 | 3/2018 | Feldman et al. |
| 2018/0110987 A1* | 4/2018 | Parker ............... A61N 1/36139 |
| 2018/0117335 A1 | 5/2018 | Parker et al. |
| 2018/0132747 A1 | 5/2018 | Parker et al. |
| 2018/0132760 A1 | 5/2018 | Parker et al. |
| 2018/0133459 A1 | 5/2018 | Parker et al. |
| 2018/0140831 A1 | 5/2018 | Feldman et al. |
| 2018/0228391 A1 | 8/2018 | Parker et al. |
| 2018/0228547 A1 | 8/2018 | Parker et al. |
| 2018/0256052 A1 | 9/2018 | Parker et al. |
| 2018/0353760 A1 | 12/2018 | Bonnet |
| 2019/0099602 A1 | 4/2019 | Esteller et al. |
| 2019/0168000 A1* | 6/2019 | Laird-Wah ......... A61N 1/37264 |
| 2019/0175915 A1 | 6/2019 | Brill et al. |
| 2019/0209844 A1 | 7/2019 | Esteller et al. |
| 2019/0275331 A1 | 9/2019 | Zhu |
| 2019/0290900 A1 | 9/2019 | Esteller et al. |
| 2019/0299006 A1 | 10/2019 | Marnfeldt |
| 2019/0366094 A1 | 12/2019 | Esteller et al. |
| 2020/0155019 A1 | 5/2020 | Esteller et al. |
| 2020/0305745 A1 | 10/2020 | Wagenbach et al. |
| 2021/0093862 A1 | 4/2021 | Vervoorderdonk et al. |

FOREIGN PATENT DOCUMENTS

| | | |
|---|---|---|
| WO | 2017/173493 | 10/2017 |
| WO | 2017/210352 | 12/2017 |
| WO | 2017/219096 | 12/2017 |

OTHER PUBLICATIONS

Brown, Glen D., et al., "Independent Component Analysis at the Neural Cocktail Party," Trends in Neurosciences, vol. 24, No. 1, Jan. 2001, 54-63.

Chen, Yonghong, et al., "Current Source Density Analysis of Ongoing Neural Activity: Theory and Application," Electrophysilogal Recording Techniques, Neuromethods, vol. 54, 2011, 15 pages.

Gray, Richard A., et al., "Quantification of Transmembrane Currents During Action Potential Propagation in the Heart," Biophysical Journal, vol. 104, Jan. 2013, 268-278.

Jirsa, V.K., et al., "A Theoretical Model of Phase Transitions in the Human Brain," Biol. Cybern., 71, 27-35 (1994).

Lee, Dongchul, et al., "Predicted Effects of Pulse Width Programming in Spinal Cord Stimulation: A Mathematical Modeling Study," Med. Biol. Eng. Comput., (2011) 49:765-774.

Riibsamen, R., et al., "Principal Component Analysis Applied to Action Potentials Reveals Neuronal Interaction in Auditory Brainstem Nuclei," Phychophysical and Physiological Advances in Hearing, Whurr Publishers, London, 1998, 352-358.

H. Mino & J. Rubenstein, "Effects of Neural Refractoriness on Spatio-Temporal Variability in Spike Initiations with Eletrical Stimulation," IEEE Trans. on Neural Sys. & Rehabilitation Eng., vol. 14, No. 3, pp. 273-280 (2006).

M. Moffit et al., A Novel 3-Dimensional Algorithm for Model-Based Programming in Spinal Cord Stimuation (SCS): Illumina-3D™, presentation (2013).

M. Hughes, "Fundamentals of Clinical ECAP Measures in Cochlear Implants: Part 1: Use of the ECAP in Speech Processor Programming (2nd Ed.)," Audiology Online (Nov. 8, 2010) (http://www.audiologyonline.com/articles/fundamentalsclinicalecapmeasuresin846).

I. Akhoun et al., "Electrically evoked compound action potential artifact rejection by independent component analysis: Technique validation," Hearing Research 302, pp. 60-73 (2013).

J. Rubinstein et al., "Pseudospontaneous activity: stochastic independence of auditory nerve fibers with electrical stimulation," Hear Res., 127(1-2), pp. 108-118 (1999) (abstract only).

J. Paz, "Physiological Midline Mapping Based on Spinal Cord Stimulation (SCS) Response Using the 32-Contact Paddle Lead," 19th NANS Annual Meeting (Dec. 13-15, 2015).

E.L. Air et al., "Electrophysiologic Monitoring for Placement of Laminectomy Leads for Spinal Cord Stimulation Under General Anesthesia," Neuromodulation: Technology at the Neural Interface, vol. 15(6), pp. 573-580 (2012).

(56) References Cited

OTHER PUBLICATIONS

J.L. Shils et al., "Intraoperative Neurophysiologic Methods for Spinal Cord Stimulator Placement Under General Anesthesia," Neuromodulation: Technology at the Neural Interface, vol. 15(6), pp. 560-572 (2012).
A. Taghva et al., "Intraoperative Electromyography as an Adjunct to Sacral Neuromodulation for Chronic Pelvic Pain," Neuromodulation: Technology at the Neural Interface, vol. 18(1), pp. 62-66 (2015).
International Search Report and Written Opinion regarding corresponding PCT Application No. PCT/US2019/020572, dated May 15, 2019.

\* cited by examiner

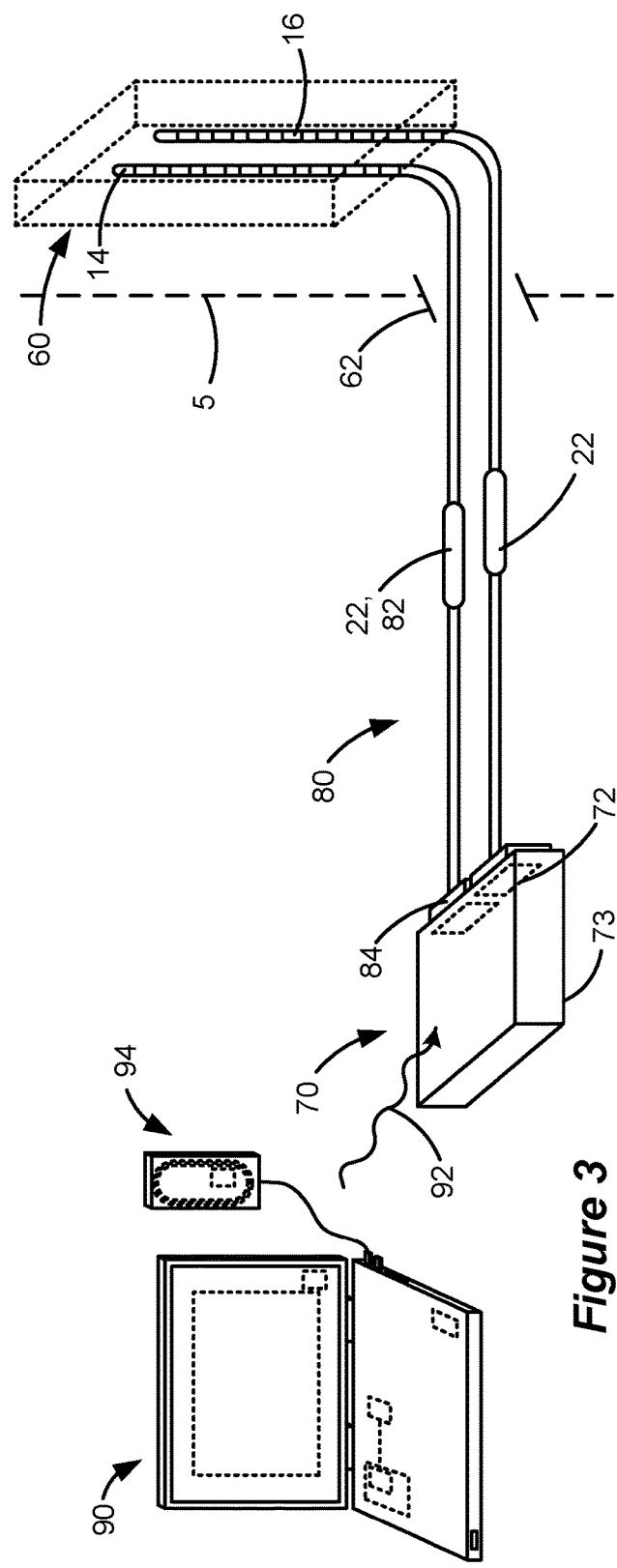
*Figure 3*
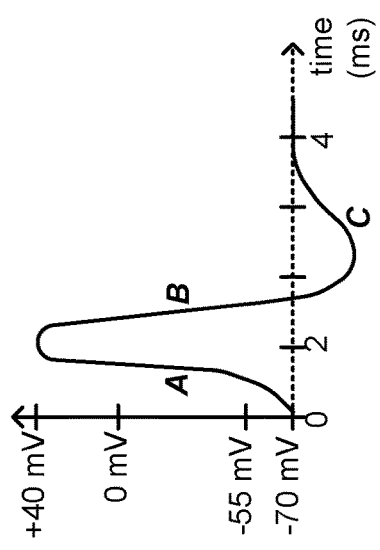
*Figure 5A*
*Figure 5B*
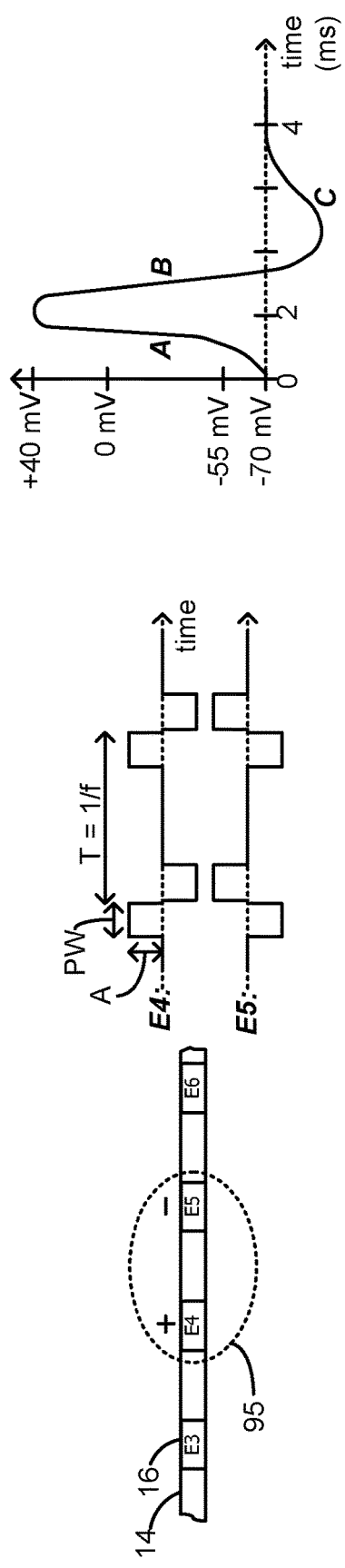
*Figure 6*

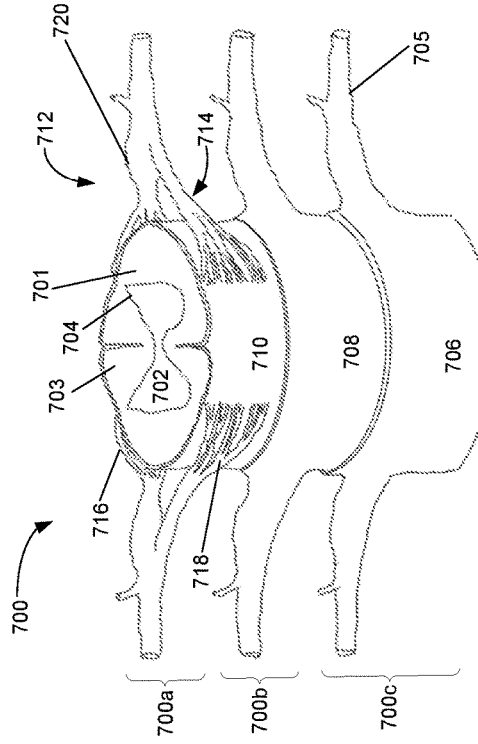
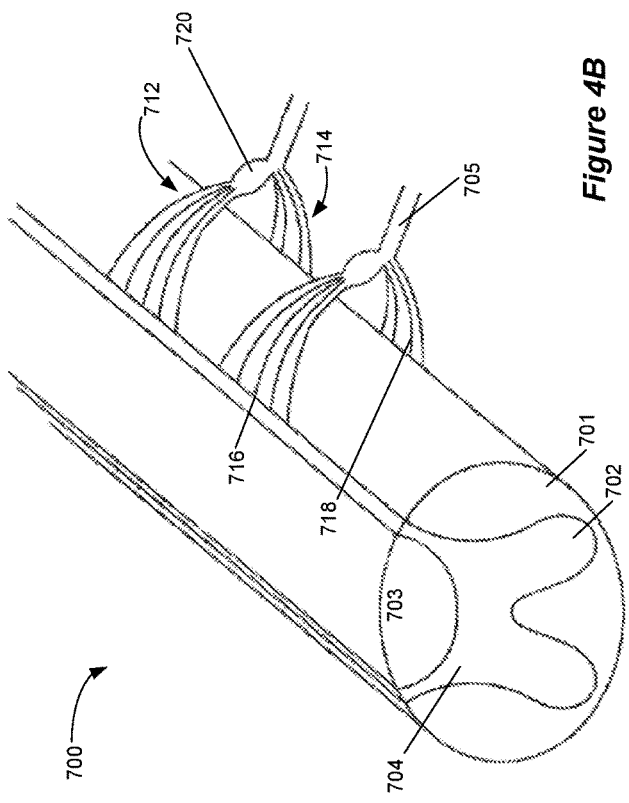

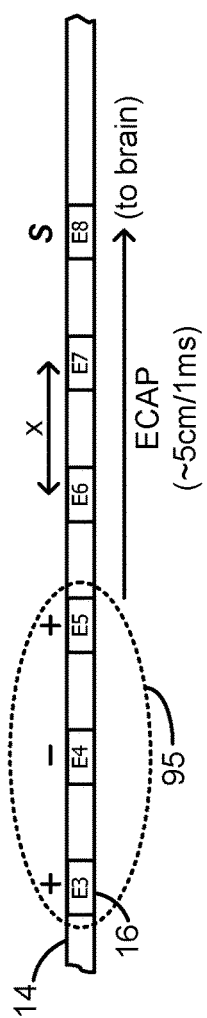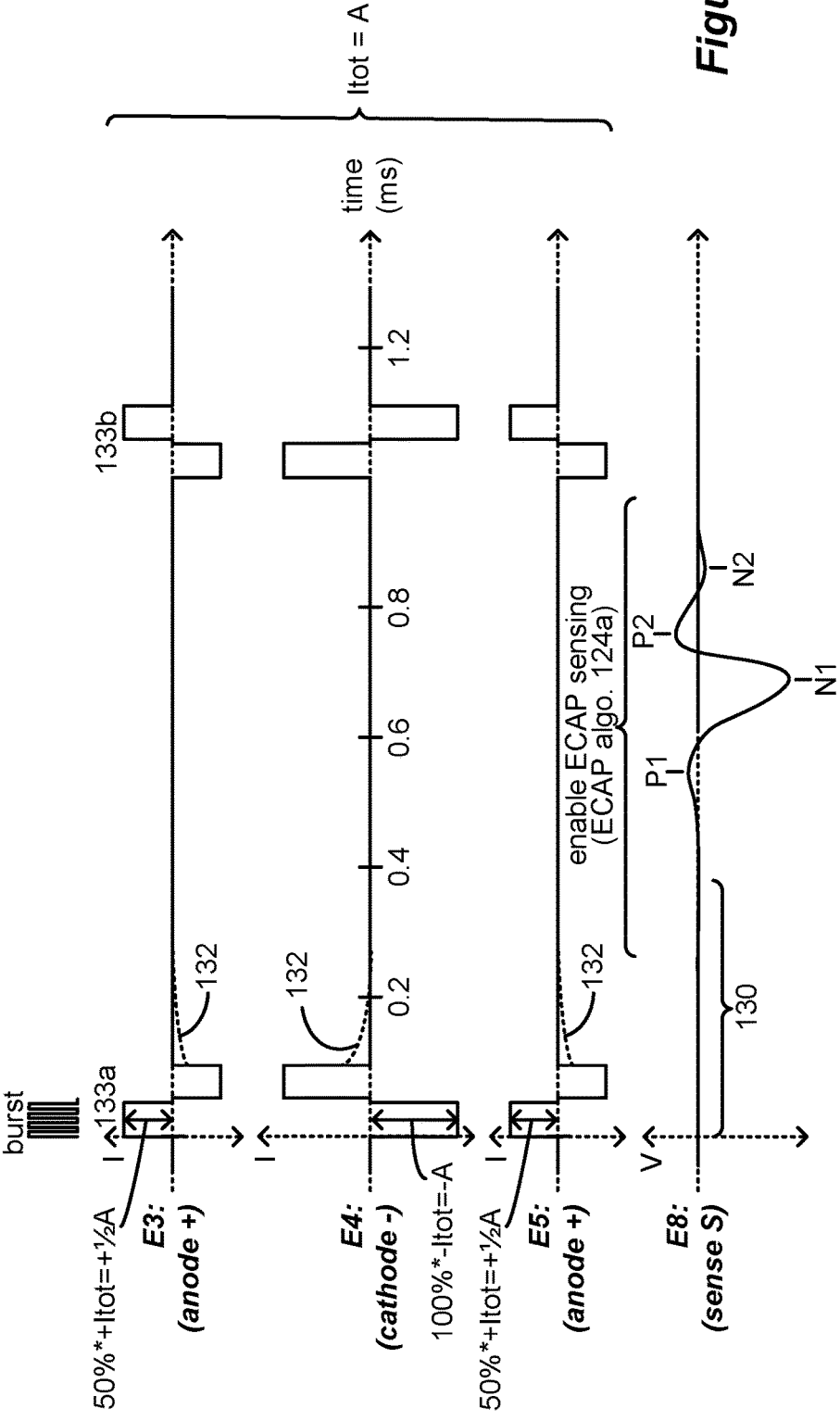
Figure 7A
Figure 7B

NEURAL STIMULATION WITH DECOMPOSITION OF EVOKED COMPOUND ACTION POTENTIALS

CROSS REFERENCE TO RELATED APPLICATIONS

This is a continuation application of U.S. patent application Ser. No. 16/291,923, filed Mar. 4, 2019 (abandoned), which is a non-provisional application of U.S. Provisional Patent Application Ser. No. 62/641,748, filed Mar. 12, 2018. These applications are incorporated herein by reference in their entireties, and priority is claimed to them.

FIELD OF THE INVENTION

The present invention relates generally to medical device systems, and more particularly to pulse generator systems operable to measure compound action potentials (CAPs), which can be used to assess and adjust stimulation therapy.

INTRODUCTION

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and Deep Brain Stimulators (DBS) to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any Implantable Medical Device (IPG) or in any IPG system, such as in a Deep Brain Stimulation (DBS) system as disclosed in U.S. Pat. No. 9,119,964.

An SCS system typically includes an Implantable Pulse Generator (IPG) 10 shown in plan and cross-sectional views in FIGS. 1A and 1B. The IPG 10 includes a biocompatible device case 30 is configured for implantation in a patient's tissue that holds the circuitry and battery 36 (FIG. 1B) necessary for the IPG to function. The IPG 10 is coupled to electrodes 16 via one or more electrode leads 14 that form an electrode array 12. The electrodes 16 are configured to contact a patient's tissue and are carried on a flexible body 18, which also houses the individual lead wires 20 coupled to each electrode 16. The lead wires 20 are also coupled to proximal contacts 22, which can be inserted into lead connectors 24 fixed in a header 28 on the IPG 10, which header can comprise an epoxy for example. Once inserted, the proximal contacts 22 connect to header contacts 26 in the lead connectors 24, which are in turn coupled by electrode feedthrough pins 34 through an electrode feedthrough 32 to circuitry within the case 30 (connection not shown).

In the illustrated IPG 10, there are thirty-two lead electrodes (E1-E32) split between four leads 14 (referred to as percutaneous leads), with the header 28 containing a 2×2 array of lead connectors 24 to receive the leads' proximal ends. However, the number of leads and electrodes in an IPG is application specific and therefore can vary. In a SCS application, the electrode leads 14 are typically implanted proximate to the dura in a patient's spinal cord, and when a four-lead IPG 10 is used, these leads can be split with two on each of the right and left sides. The proximal contacts 22 are tunneled through the patient's tissue to a distant location such as the buttocks where the IPG case 30 is implanted, at which point they are coupled to the lead connectors 24. As also shown in FIG. 1A, one or more flat paddle leads 15 can also be used with IPG 10, and in the example shown thirty-two electrodes 16 are positioned on one of the generally flat surfaces of the head 17 of the paddle lead, which surface would face the dura when implanted. In other IPG examples designed for implantation directly at a site requiring stimulation, the IPG can be lead-less, having electrodes 16 instead carried by the case of the IPG for contacting the patient's tissue.

As shown in the cross section of FIG. 1B, the IPG 10 includes a printed circuit board (PCB) 40. Electrically coupled to the PCB 40 are the battery 36, which in this example is rechargeable; other circuitry 46 coupled to top and/or bottom surfaces of the PCB 40, including a microcontroller or other control circuitry necessary for IPG operation; a telemetry antenna—42a and/or 42b—for wirelessly communicating data with an external controller 50 (FIG. 2); a charging coil 44 for wirelessly receiving a magnetic charging field from an external charger (not shown) for recharging the battery 36; and the electrode feedthrough pins 34 (connection to circuitry not shown). If battery 36 is permanent and not rechargeable, charging coil 44 would be unnecessary.

The IPG 10 also includes one or more antennas 42a and 42b for transcutaneously communicating with external programming devices, such as a patient external controller 50 (FIG. 2), or a clinician programmer 90 (FIG. 3). Antennas 42a and 42b are different in shape and in the electromagnetic fields they employ. Telemetry antenna 42a comprises a coil, which can bi-directionally communicate with an external device via a magnetic induction communication link. Telemetry antenna 42b comprises a short-range Radio-Frequency (RF) antenna that operates in accordance with a short-range RF communication standard, such as Bluetooth, BLE, NFC, Zigbee, WiFi (802.11x), and the Medical Implant Communication Service (MICS) or the Medical Device Radiocommunications Service (MDRS).

Implantation of IPG 10 in a patient is normally a multistep process, as explained with reference to FIG. 3. A first step involves implantation of the distal ends of the lead(s) 14 or 15 with the electrodes 16 into the spinal column 60 of the patient through a temporary incision 62 in the patient's tissue 5. (Only two leads 14 with sixteen total electrodes 16 are shown in FIG. 3 for simplicity). The proximal ends of the leads 14 or 15 including the proximal contacts 22 extend externally from the incision 62 (i.e., outside the patient), and are ultimately connected to an External Trial Stimulator (ETS) 70. The ETS 70 is used during a trial stimulation phase to provide stimulation to the patient, which may last for two or so weeks for example. To facilitate the connection between the leads 14 or 15 and the ETS 70, ETS extender cables 80 may be used that include receptacles 82 (similar to the lead connectors 24 in the IPG 10) for receiving the proximal contacts 22 of leads 14 or 15, and connectors 84 for meeting with ports 72 on the ETS 70, thus allowing the ETS 70 to communicate with each electrode 16 individually. Once connected to the leads 14 or 15, the ETS 70 can then be affixed to the patient in a convenient fashion for the duration of the trial stimulation phase, such as by placing the ETS 70 into a belt worn by the patient (not shown). ETS 70 includes a housing 73 for its control circuitry, antenna, etc., which housing 73 is not configured for implantation in a patient's tissue.

The ETS 70 essentially mimics operation of the IPG 10 to provide stimulation to the implanted electrodes 16, and thus includes contains a battery within its housing along with stimulation and communication circuitry similar to that provided in the IPG 10. Thus, the ETS 70 allows the effectiveness of stimulation therapy to be verified for the patient, such as whether therapy has alleviated the patient's symptoms (e.g., pain). Trial stimulation using the ETS 70 further allows for the determination of particular stimulation program(s) that seems promising for the patient to use once the IPG 10 is later implanted into the patient. A stimulation program may include stimulation parameters that specify for example: which of the electrodes 16 are to be active and used to issue stimulation pulses; the polarity of those active electrodes (whether they are to act as anodes or cathodes); the current or voltage amplitude (A) of the stimulation pulses; the pulse width (PW) of the stimulation pulses; the frequency (f) of the stimulation pulses; the duty cycle (DC) of the stimulation pulses (i.e., the percentage of time that the pulses are asserted relative to the period of the pulses) the shape of the stimulation waveform (e.g., one or more square pulses, one or more ramped pulses, one or more sinusoidal pulses, or even non-pulse-based waveforms, etc.); and other parameters related to issuing a burst of pulses, such as the number of pulses; etc.

The stimulation program executed by the ETS 70 can be provided or adjusted via a wired or wireless link 92 (wireless shown) from a clinician programmer 90. As shown, the clinician programmer 90 comprises a computer-type device, and may communicate wirelessly with the ETS 70 via link 92, which link may comprise magnetic inductive or short-range RF telemetry schemes as already described. Should the clinician programmer 90 lack a communication antenna, a communication head or wand 94 may be wired to the computer which has a communication antenna. Thus, the ETS 70 and the clinician's programmer 90 and/or its communication head 94 may include antennas compliant with the telemetry scheme chosen. Clinician programmer 90 may be as described in U.S. Patent Application Publication 2015/0360038. External controller 50 (FIG. 2) may also communicate with the ETS 70 to allow the patient means for providing or adjusting the ETS 70's stimulation program.

At the end of the trial stimulation phase, a decision is made whether to abandon stimulation therapy, or whether to provide the patient with a permanent IPG 10 such as that shown in FIGS. 1A and 1B. Should it be determined that stimulation therapy is not working for the patient, the leads 14 or 15 can be explanted from the patient's spinal column 60 and incision 62 closed in a further surgical procedure.

By contrast, if stimulation therapy is effective, IPG 10 can be permanently implanted in the patient as discussed above. ("Permanent" in this context generally refers to the useful life of the IPG 10, which may be from a few years to a few decades, at which time the IPG 10 would need to be explanted and a new IPG 10 implanted). Thus, the IPG 10 would be implanted in the correct location (e.g., the buttocks) and connected to the leads 14 or 15, and then temporary incision 62 can be closed and the ETS 70 dispensed with. The result is fully-implanted stimulation therapy solution. If a particular stimulation program(s) had been determined during the trial stimulation phase, it/they can then be programmed into the IPG 10, and thereafter modified wirelessly, using either the external programmer 50 or the clinician programmer 90.

SUMMARY

Some embodiments described herein provide a device comprising: a microprocessor programmed to: cause a first electrode implanted in a patient to issue a stimulation waveform to the patient's neural tissue, receive a signal from a second electrode implanted in the patient, the signal indicative of a neural response to the stimulation waveform, compare the received signal to a modeled neural response generated using responses of a plurality of modeled neural elements and weights associated with each modeled neural element, and adjust the modeled neural response based on the comparison. Adjusting the modeled neural response may comprise adjusting the plurality of modeled neural elements or adjusting the parameters or weights associated with at least one of the neural elements. The modeled neural response may comprise a computed transmembrane current associated with each of the plurality of modeled neural elements. The modeled neural response may comprise a modeled voltage induced by the transmembrane currents. The modeled neural response may be a weighted summation of the modeled voltages. The microprocessor may be further programmed to estimate relative recruitment of the neural elements within the patient based on the comparison. The microprocessor may be further programmed to adjust the stimulation waveform to selectively recruit a subset of the patient's neural elements. Adjusting the stimulation waveform may comprise adjusting one or more of an amplitude, pulse width, pulse rate, or pulse shape of the stimulation waveform. The modeled neural elements may comprise modeled neural fibers of a spinal column. The modeled neural response may comprise a modeled evoked compound action potential (ECAP).

Further embodiments provide a non-transitory computer-readable medium comprising instructions configured to cause a microprocessor to: receive a signal from an electrode implanted in a patient, the signal indicative of a neural response of the patient to a stimulation waveform, provide a modeled neural response based on a baseline set of modeled neural elements, compare the modeled neural response to the received signal, and adjust the modeled neural response based on the comparison. Providing a modeled neural response may comprise: determining transmembrane currents for each of the modeled neural elements, associating a weight with each of the transmembrane currents, determining a voltage induced by the transmembrane currents, and determining the modeled neural response as a weighted sum of the voltages for the transmembrane currents. Adjusting the modeled neural response may comprise adding neural elements to the baseline set of modeled neural elements. Adjusting the modeled neural response may comprise adjusting the weights associated with the transmembrane currents. Adjusting the modeled neural response may comprise adjusting one or more parameters of the baseline set of modeled neural elements. The one or more parameters of the baseline set of modeled neural elements may be selected from the group consisting of geometry of the modeled neural element, physiology of the modeled neural element, and electrical properties of the neural elements. Receiving a signal from an electrode implanted in a patient may comprise receiving a first signal from a first electrode and receiving a second signal from a second electrode. Receiving a signal from an electrode implanted in a patient may comprise receiving a first signal from the electrode indicative of the neural response at a first time and receiving a second signal from the electrode indicative of the neural response at a second time. The non-transitory computer-readable medium may further comprise instructions to cause the microprocessor to identify a preferred stimulation waveform based on the received signal. The non-transitory computer-readable medium may further comprise instructions to cause the microprocessor to identify a stimulation waveform associated with a side-effect based on the received signal. The non-transitory computer-readable medium may further comprise instructions to cause the microprocessor to adjust the stimulation waveform. Adjusting the stimulation waveform may comprise adjusting one or more of an amplitude, pulse width, pulse rate, or pulse shape of the stimulation waveform.

Some embodiments provide a method of controlling neuromodulation of a patient, the method comprising: comparing a neural response of the patient to a modeled neural response, wherein the comparison indicates a neural recruitment in response to the neuromodulation, identifying a neural recruitment correlated to a therapeutic effect, and adjusting the neuromodulation to adjust the identified neural recruitment, wherein the modeled neural response is provided by: determining transmembrane currents for each of a baseline set of modeled neural elements, associating a weight with each of the transmembrane currents, determining a voltage induced by the transmembrane currents, and determining the modeled neural response as a weighted sum of the voltages for the transmembrane currents. The identified neural recruitment may be associated with a therapeutic effect and the adjusting neuromodulation may maintain or enhance the identified neural recruitment. The identified neural recruitment may be associated with a side-effect and the adjusting neuromodulation may suppress the identified neural recruitment.

Further embodiments provide a neuromodulation system comprising: a first device comprising a non-transitory computer-readable medium, comprising instructions to cause a microprocessor to: receive a signal from an electrode implanted in a patient, the signal indicative of a neural response of the patient to a stimulation waveform, provide a modeled neural response based on a baseline set of modeled neural elements, compare the received signal to the modeled neural response, and adjust the modeled neural response based on the comparison. Providing a modeled neural response may comprise: determining transmembrane currents for each of the modeled neural elements, associating a weight with each of the transmembrane currents, determining a voltage induced by the transmembrane currents, and determining the modeled neural response as a weighted sum of the voltages for the transmembrane currents. Adjusting the modeled neural response based on the comparison may comprise adjusting the plurality of modeled transmembrane currents or adjusting the weights associated with at least one of the transmembrane currents. The non-transitory computer-readable medium may further comprise instructions to cause a microprocessor to adjust the stimulation waveform based on the comparison. The non-transitory computer-readable medium may further comprise instructions to cause a microprocessor to determine a neural recruitment based on the comparison. The non-transitory computer-readable medium may further comprise instructions to cause a microprocessor to adjust the stimulation waveform to maintain the determined neural recruitment. The first device may be an external programmer for an implantable pulse generator (IPG) or an external trial stimulator (ETS). The neuromodulation system may further comprise an IPG or an ETS configured to provide the stimulation waveform to one or more electrodes implanted in the patient. The first device may be an IPG or an ETS.

BRIEF DESCRIPTION OF THE DRAWINGS

FIG. 3 shows a clinician programming system for communicating with an IPG or an External Trial Stimulator (ETS).

FIGS. 4A and 4B show aspects of the spinal cord and related neural anatomy

FIGS. 5A and 5B show a stimulation waveform.

FIG. 6 shows a graph of an action potential of a neuron.

FIGS. 7A and 7B show a stimulation waveform and an evoked compound action potential.

DESCRIPTION

Figure 1A:
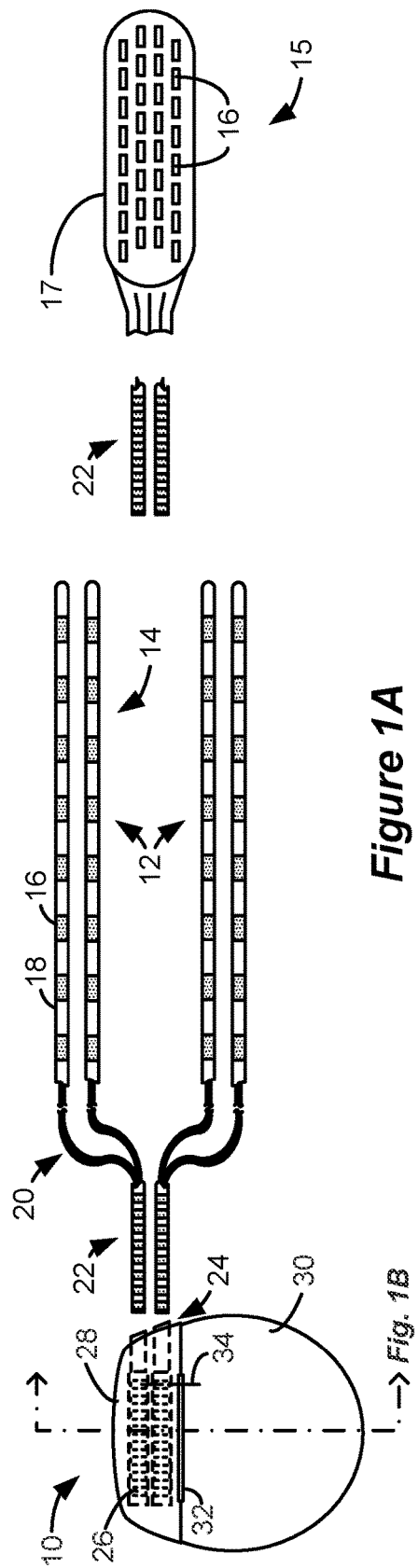
FIGS. 1A and 1B respectively show an Implantable Pulse Generator (IPG) in plan and cross-sectional views.
Figure 1B:
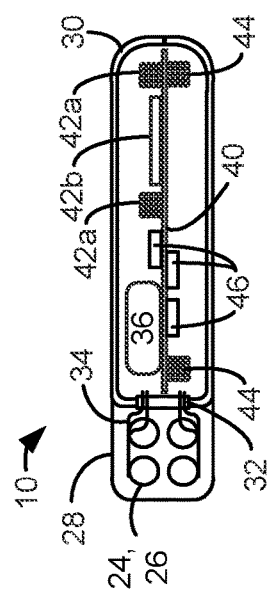

Various embodiments described herein involve neural stimulation. Examples include spinal cord modulation, i.e., spinal cord stimulation (SCS) as well as stimulation and sensing of related neural anatomy. Additional embodiments may include deep brain stimulation (DBS), peripheral nerve stimulation (PNS), and the like. Focusing on SCS, a brief description of the anatomy and physiology of the spinal cord is provided herein to assist the reader. FIGS. 4A and 4B illustrate, by way of example, a portion of a spinal cord 700 including white matter 701 and gray matter 702 of the spinal cord. A typical transverse section of the spinal cord includes a central "butterfly" shaped central area of gray matter 702 substantially surrounded by an ellipse-shaped outer area of white matter 701. The white matter of the dorsal column (DC) 703 includes mostly large myelinated axons that form afferent fibers that run in an axial direction. The dorsal portions of the "butterfly" shaped area of gray matter are referred to as dorsal horns (DH) 704. In contrast to the DC fibers that run in an axial direction, DH fibers can be oriented in many directions, including laterally with respect to the longitudinal axis of the spinal cord. The gray matter 702 includes cell bodies, synapse, dendrites, and axon terminals.

Referring to FIG. 4A, the spinal cord is enclosed within three layers of tissue, collectively called the meninges. The outer layer of the meninges, called the dura mater 706, is shown in spinal cord segment 700c. The dura mater has been removed in spinal cord segment 700b to reveal the middle meninges, called the arachnoid 708. The innermost meninges, the pia mater 710, is shown in spinal cord segment 700a.

Examples of spinal nerves 705 are also illustrated. Upon removal of the meningeal layers, it is seen that each spinal nerve 705 splits into a dorsal root (DR) 712 and a ventral root 714, each of which comprise subdivisions referred to as rootlets. In FIG. 4A, the dorsal rootlets are labeled 716 and the ventral rootlets are labeled 718. The dorsal root also includes a structure called the dorsal root ganglion (DRG) 720, which comprises cell bodies of the afferent neurons. The dorsal root 712 contains afferent neurons, meaning that they carry sensory signals into the spinal cord, and the ventral root 714 functions as an efferent motor root. The dorsal and ventral roots join to form mixed spinal nerves 705.

An example of stimulation pulses as prescribed by an example stimulation program and as executable by the IPG or ETS 70 is illustrated in FIGS. 5A and 5B. As shown in FIG. 5A, electrode E4 is selected as the anode and electrode E5 is selected as the cathode. FIG. 5B illustrates the waveforms of the stimulation pulses delivered by E4 and E5. In the example shown, each stimulation pulse is biphasic, meaning it comprises a first pulse phase followed essentially immediately thereafter by an opposite polarity pulse phase. The pulse width (PW) could comprise the duration of either of the pulse phases individually as shown, or could comprise the entire duration of the biphasic pulse including both pulse phases. The frequency (f) and amplitude (A) of the pulses is also shown. Although not shown, monophasic pulses—having only a first pulse phase but not followed by an active-charge recovery second pulse phase—can also be used. Likewise, charge imbalanced biphasic pulses may be used, wherein the two phases are not symmetric. The pulses as shown comprise pulses of constant current, and notice that the amplitude of the current at any point in time is equal but opposite such that current injected into the patient's tissue by one electrode (e.g., E4) is removed from the tissue by the other electrode (E5). Notice also that the area of the first and second pulses phases are equal, ensuring active charge recovery of the same amount of charge during each pulse phase. Although not shown, more than two electrodes can be active at any given time. For example, electrode E4 could comprise an anode providing a +10 mA current pulse amplitude, while electrodes E3 and E5 could both comprise cathodes with −7 mA and −3 mA current pulse amplitudes respectively. Biphasic pulses are particularly beneficial when pulses are issued at higher frequencies, although they may be used at lower frequencies as well.

When a neural element is recruited by electrical stimulation, it will generate an action potential—that is, the neural fiber will "fire." An action potential for a typical neural fiber is shown in FIG. 6. Should electrical recruitment from electrical stimulation cause the neural fiber's membrane potential increase from a resting state (e.g., −70 mV as measured from inside the cell) to exceed a threshold (e.g., −55 mV), the neural fiber will be depolarized ("A"). If electrical stimulation causes the neural fiber's membrane potential decrease from the resting state to a more negative potential, the neural fiber will be hyperpolarized ("C"). At the end of depolarization, the neural fibers membrane potential returns to the resting status, the neural fiber will be repolarize ("B"), which may result in a depolarization before coming to rest again. If electrical stimulation continues, the neural fiber will fire again at some later time, though the neural fiber cannot fire again until after the refractory period where the neuron cannot be responsive to any stimuli following the depolarization and repolarization event. Note that the action potential may not change in magnitude for a given location along a given neural fiber. Instead, changing the strength of stimulation may affect the frequency at which action potentials are issued, the shape of the action potential, and may also affect the population of neural elements, such as the type and shape of the neural elements that are recruited. Each neural fiber is unique in its shape and size, and thus can fire at its own inherent maximum frequency.

Various mechanisms of action underlying pain relief may exist. Some believe that the perception of pain signals is inhibited via the gate control theory of pain, which suggests that enhanced activity of innocuous touch or pressure afferents via electrical stimulation induce activation of interneurons within the DH 704 of the spinal cord that releases inhibitory neurotransmitters (Gamma-Aminobutyric Acid (GABA), glycine), which in turn reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been targeted for stimulation at an amplitude that provides pain relief.

Activation of large sensory DC nerve fibers in conventional SCS creates action potentials (i.e., nerve impulses) that propagate orthordromically (toward the brain) and antidromically (away from the brain) from the point of stimulation. The antidromic propagation of action potentials to fiber collaterals and terminals ending in the DH evokes pain control mechanisms within the DH, as described above. The orthodromic propagation of action potentials is responsible for the paresthesia sensation that often accompanies conventional SCS therapy.

The orthodromic and/or antidromic propagation of action potentials can be sensed at electrodes of the lead 14. Consider FIG. 7A, in which electrodes E3, E4 and E5 on lead 14 are used to produce pulses in a tripolar mode of stimulation, with E3 and E5 comprising an anode (+; or source of current) and E4 a cathode (−; or sink of current). Such stimulation produces an electromagnetic (EM) field in a volume 95 of the patient's tissue around the selected electrodes. Some of the neural fibers within the EM field volume 95 will be recruited and fire, particularly those proximate to the cathodic electrode E4. The sum of the neural fibers firing within volume 95 will mask signals indicative of pain in an SCS application, thus providing the desired therapy.

The stimulation program is defined as before by various stimulation parameters to form stimulation pulses, such as which electrodes are active for stimulation, the polarity of those electrodes, the amplitude at selected electrodes, pulse width, pulse frequency or pulse to pulse interval, and stimulation waveform shape (square pulses in the example shown), although these parameters are not all labeled in FIG. 7B. In the example stimulation program shown, and considering only the first phase of the biphasic pulses, electrode E4 is selected to operate as a cathode (−), and electrodes E3 and E5 are selected to operate an anodes (+). Such stimulation is usually referred to as tripolar stimulation. Tripolar stimulation is one preferred mode of providing stimulation, particularly in an SCS application, because neural fibers in the dorsal column are activated proximate to the cathode. Tripolar stimulation generally allows effective stimulation to occur at lower current amplitudes.

In the example shown, the pulses are defined with respect to a total anodic and cathodic current (collectively, Itot) that the electrodes will provide at any given time. This is desirable so that the patient's tissue will not receive a net amount of charge. The sole cathode electrode E4 provides all the total cathodic current (−Itot), and so provides 100*−Itot, or −A. The two anode electrodes E3 and E5 must together issue the total anodic current (+Itot), and in this example each provides 50%*+Itot, or +A/2. The anode electrodes can issue any anodic current combination that together will equal +Itot (e.g., 70%*+Itot and 30%*+Itot). It is assumed that such stimulation program has been chosen as one that generally provides good therapeutic results for a particular patient.

Neural fibers recruited and that fire within volume 95 create a cumulative response called an Evoked Compound Action Potential, or ECAP. The ECAP is a summation of the individual action potentials (such as shown in FIG. 6) of each of the recruited neural elements.

Once stimulation begins (at time=0), an ECAP will be produced comprising the sum of the action potentials of neural fibers recruited and hence firing in volume 95. As shown in FIG. 7B, the ECAP will propagate along neural fibers via neural conduction with speeds of about 3.5-7.5 cm/ms in the typical case of Aβ fibers, or 0.3-3.5 cm/ms in the case of Aδ fibers. In the example shown, the ECAP moves to the right, which is in an orthodromic direction toward the brain (rostrally). However, the ECAP will also move in the antidromic direction as well toward the bottom of the spinal cord of the patient (caudally). The amplitude of the ECAP will depends on the number and type of neural fibers that are firing. Amplitude of ECAP can be evaluated by the magnitude of peak P1, or the magnitude between peak P1 and valley N1. Generally speaking, a primary ECAP response, e.g., the height of peak P1, can vary, usually between tens of microVolts to tens of milliVolts.

It should be noted here that compound action potentials may be evoked in various neural elements, including the neural fibers of the dorsal column, the dorsal root fibers, the dorsal root ganglia, peripheral nerves etc. As used herein, the ECAP refers to action potentials evoked in any of the neural elements.

It should also be noted here that each of the individual action potentials that contribute to the ECAP may not move at the same velocity through the patient's tissue. For example, action potentials associated with larger fibers typically propagate at a higher velocity than those associated with smaller fibers. This is discussed in more detail below.

Referring again to FIGS. 7A and 7B, a single sense electrode (S) has been chosen to sense the ECAP as it moves past, which in this example is electrode E8. Selection of an appropriate sense electrode can be determined by an ECAP algorithm operable in the control circuitry of the IPG based on a number of factors. For example, it is preferable that a sense electrode S be sensibly chosen with respect to the active electrodes, such that the EM field produced around the active electrodes will dissipate (or more preferably, cease) at the sense electrode by the time the ECAP arrives. This simplifies ECAP detection at the sense electrode, because voltages present in the EM field will not interfere with and potentially mask the ECAP at the sense electrode. (Note that the stimulation artifact resulting from the EM field is not shown at the sense electrode E8 for simplicity). To choose a sense electrode, the ECAP algorithm (described below) preferably knows the pulse width of the pulses being issued, the extent of the size of the EM field (which can be estimated), the speed at which the ECAP is expected to travel, and the distance (x) between electrodes 16 in the electrode array 12, e.g., along a particular straight lead 14 or a paddle lead 15 (FIG. 1A).

In FIGS. 7A and 7B, for example, assume that the pulse width (of both phases of the biphasic pulses) is 0.1 ms as shown, and that sense electrode E8 is generally 2.0 cm away from the active electrodes (and hence their EM field). When the ECAP starts to form at time=0, it will arrive at electrode E8 after some delay 130 in accordance with the speed at which the ECAP moves (e.g., 5 cm/1 ms). In this example, the ECAP will start to pass sense electrode E8 at 0.4 ms.

Thus, the ECAP algorithm can thus enable sensing of the ECAP starting at or before time=0.4 ms after the start of the stimulation pulse. Sensing can last for as long as necessary to detect at least some aspects of the shape and size of the resulting ECAP. For example, sensing can last for a long enough time to allow the polarization and refraction peaks in the ECAP to be detected, which may comprise up to 3 ms for example. If the total duration of the ECAP is longer than the quiet period between two subsequent pulses, e.g., between pulses 133a and 133b, subsequent pulses 133b may not be enabled until the ECAP measurement has finished.

Figure 8:
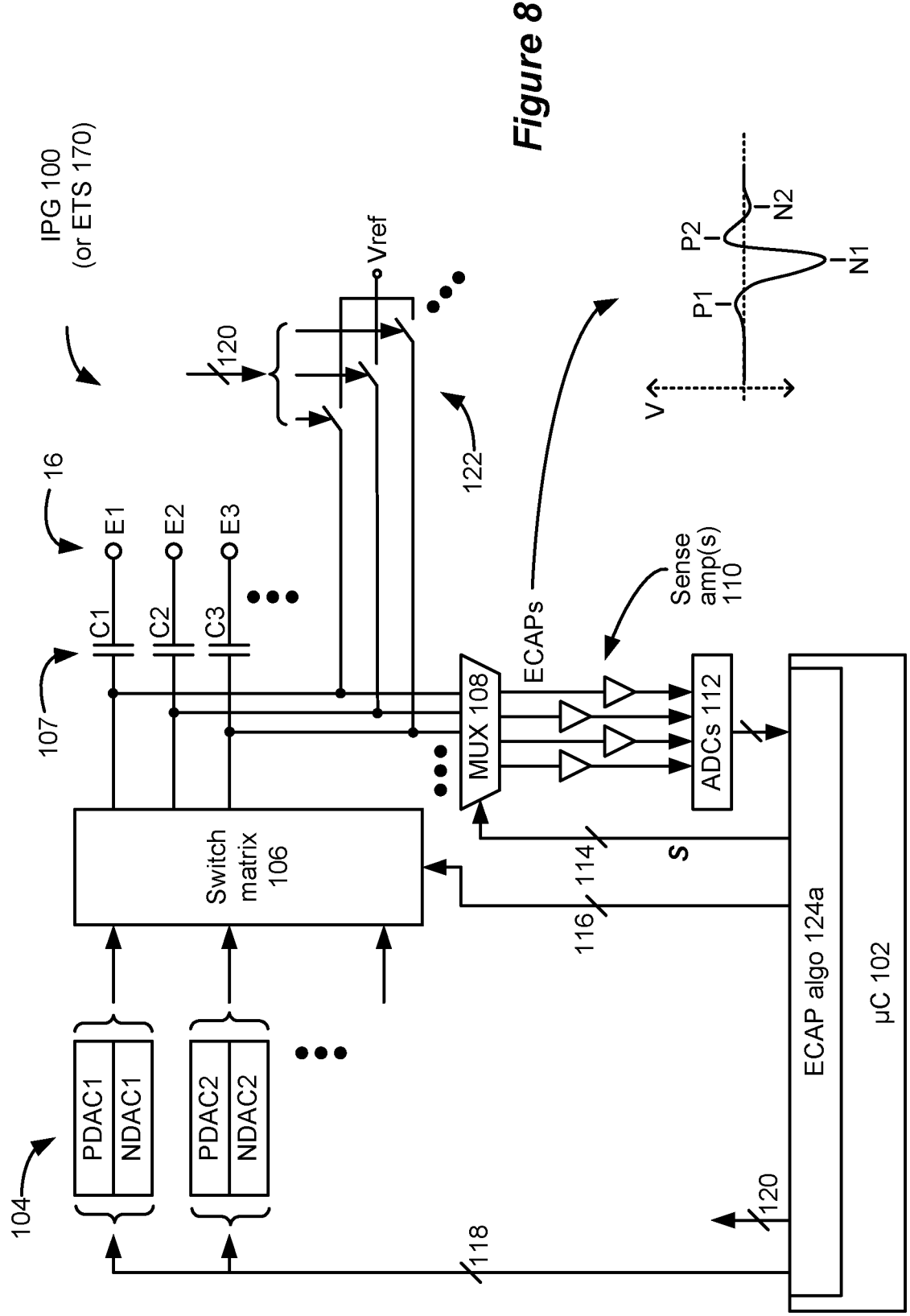
FIG. 8 shows aspects of circuitry for sensing ECAPs and modifying stimulation based on an algorithm using ECAP parameters.

FIG. 8 shows circuitry for an improved IPG 100 operable with the disclosed technique for sensing ECAP and using the sensed ECAP as a biomarker for directing therapy, as described further below. Although described in the context of an IPG 100, it should be realized that the disclosed technique could also be operable in an improved external stimulator, such as an External Trial Stimulation 170 that generally mimics the operation of an IPG as explained earlier.

The IPG 100 (or ETS 170) includes control circuitry 102 into which an ECAP algorithm 124a can be programmed. Control circuitry 102 may comprise a microcontroller for example such as Part Number MSP430, manufactured by Texas Instruments, which is described in data sheets at http://www.ti.com/lsds/ti/microcontroller/16-bit_msp430/overview.page?DCMP=MCU_other& HQS=msp430, which is incorporated herein by reference. Other types of control circuitry may be used in lieu of a microcontroller as well, such as microprocessors, FPGAs, DSPs, or combinations of these, etc. Control circuitry 102 may also be formed in whole or in part in one or more Application Specific Integrated Circuits (ASICs), as described in U.S. Patent Application Publication 2012/0095529 and U.S. Pat. Nos. 9,061,140 and 8,768,453, which are incorporated herein by reference.

In the IPG 100 (or ETS 170) a bus 118 provides digital control signals to one or more Digital-to-Analog converters (DACs) 104, which are used to produce currents or voltages of prescribed amplitudes (A) for the stimulation pulses, and with the correct timing (PW, f). As shown, the DACs include both PDACs which source current to one or more selected anode electrodes, and NDACs which sink current from one or more selected cathode electrodes. In this example, a switch matrix 106 under control of bus 116 is used to route the output of one or more PDACs and one or more NDACs to any of the electrodes, which effectively selects the anode and cathode electrodes. Buses 118 and 116 thus generally set the stimulation program the IPG 100 is running. The illustrated circuitry for producing stimulation pulses and delivering them to the electrodes is merely one example. Other approaches may be found for example in U.S. Pat. Nos. 8,606,362 and 8,620,436, and 11,040,192. Note that a switch matrix 106 isn't required, and instead a PDAC and NDAC can be dedicated to (e.g., wired to) each electrode.

Notice that the current paths to the electrodes 16 include the DC-blocking capacitors 107 alluded to earlier, which, as known, provide additional safety by preventing the inadvertent supply of DC current to an electrode and to a patient's tissue. As discussed earlier, capacitances such as these can become charged as stimulation currents are provided, providing an impetus for the use of biphasic pulses.

One or more of the electrodes 16 can be used to sense the ECAP described earlier, and thus each electrode is further coupleable to at least one sense amp 110. In the example shown, there are four sense amps 110 each corresponding to a particular timing channel in which stimulation can be issued. Under control by bus 114, a multiplexer 108 can couple any of the electrodes to any of the sense amps 110 at a given time. This is however not strictly necessary, and instead each electrode can be coupleable to its own dedicated sense amp 110, or all electrodes can be selected for sensing at different times and presented by MUX 108 to a single sense amp 110. The analog waveform comprising the ECAP, described further below, is preferably converted to digital signals by one or more Analog-to-Digital converters (ADC(s)) 112, which may sample the waveform at 50 kHz for example. The ADC(s) may also reside within the control circuitry 102, particularly if the control circuitry 102 has A/D inputs.

Notice that connection of the electrodes 16 to the sense amp(s) 110 preferably occurs through the DC-blocking capacitors 107, such that capacitors are between the electrodes and the sense amp(s) 110. This is preferred so as not to undermine the safety provided by the DC-blocking capacitors 107.

Once the digitized ECAP is received at the control circuitry 102, it is processed by the ECAP algorithm 124a to determine one or more ECAP features that describe the basic morphology (e.g. shape and size) of the ECAP(s), as explained further below with reference to FIG. 11. The response to stimulation can include potentials observed at different delays corresponding to different type of neural elements recruited. The delay from the stimulus can depend on the distance between the sensed electrode and the activation region where the electrical stimulus recruited most neural elements. Neural elements include axon fibers, neuron cell bodies, neuron dendrites, axon terminals, locations where fiber collaterals branch, interneurons, glial cells, or any nervous system functional part. In the specific case of the spinal cord, the sense electrodes can be placed over the dorsal column, more laterally in the epidural space towards and over the edge of dorsal horn and/or Lissauer's tract, over the dorsal root entry zone (DREZ), the rootlets, the dorsal root ganglia (DRG), the cauda equina region, the spinal nerves close to the spinal cord, the spino-thalamic tract, and any other of the tracts surrounding the gray matter of the spinal cord. An ECAP can contain a number of peaks or waves indicative of the different phases of the averaged or compound action potential sensed and depending on the delay with respect to the stimulus, the peak potentials can be indicative of different type of fibers activated. Axon fibers with different functions (C fibers, Aβ fibers, Aδ fibers, and others) have different diameters that correlate with different propagation velocities for the compound potentials. Conduction velocities for different axonal fiber types are known, and the conduction velocities of the ECAPs sensed in the spinal cord can be calculated to determine the originating fiber. As shown, peaks in the ECAP are conventionally labeled with P for positive peaks and N for negative peaks, with P1 comprising a first positive peak, N1 a first negative peak, P2 a second positive peak and so on. Note that not all ECAPs will have the exact shape and number of peaks as illustrated in FIG. 8 (and FIG. 11), because an ECAP's shape is a function of the number and types and distance of neural fibers that are recruited in a given volume 95.

Note that the DC blocking capacitor 107 through which the ECAPs pass will remove any DC components in the signal, which is thus referenced to 0 Volts. If necessary, the sensed ECAP signal can be amplified and level-shifted by the sense amp(s) 110 so that its voltage is within a range that the control circuitry 102 in the IPG 100 can handle, such as between 3 Volts and ground.

The inventor has discovered methods and systems that can use sensed ECAPs to direct the timing, location, and shape at which stimulation is applied to a patient's neural anatomy to maximize therapeutic response and/or minimize side effects of stimulation. In particular, the inventor has discovered that sensed ECAPs can be decomposed to identify particular neural populations that contribute to the sensed compound potential, thereby identifying which recruited neural populations/responses correlate with therapeutic effects and/or with side effects.

As mentioned above, sensed ECAPs comprise the cumulative action potentials of the neural elements recruited during a stimulation pulse. The action potentials of the various recruited neural elements may propagate at the different velocities through the patient's tissue. Typically, action potentials propagate at a higher velocity along larger fibers than along smaller fibers. For example, consider FIG. 9. A stimulation waveform produced at $E_{stim}$ (such as the stimulation waveforms illustrated in FIG. 7B) evokes action potentials 902 in neural elements near $E_{stim}$. Assume that the neural elements comprise three populations of fibers—large, medium, and small fibers. Action potentials within the population of large fibers is represented as a solid line 904. Action potentials within the population of medium fibers is represented as a solid line 906. Action potentials within the population of small fibers is represented as a solid line 908. The action potentials of the populations combine to yield a compound action potential (ECAP) 910, which propagates along the neural elements of the spinal cord 700. Because the action potentials of the three populations propagate at different rates through the neural anatomy, the action potentials for each population reaches each of the subsequent electrodes along the propagation path at different times. In other words, the compound action potential signal 910 "spreads" as it propagates because of differences in the propagation velocity of the three components of the compound signal. Assume that electrode E8 is used as a sense electrode to sense the ECAP. The shape of the ECAP signal 910 sensed at the electrode E8 is a summation of the three component action potential signals. Moreover, the shape of the ECAP signal at a given sensing electrode changes as a function of time. Electrical signals within the fastest (typically the largest) fibers reach the sensing electrode first. Thus, at the earliest time the ECAP shape is dominated by electrical activity within the larger fibers. As time progresses, the smaller fibers influence the shape of the ECAP signal.

Figure 9:
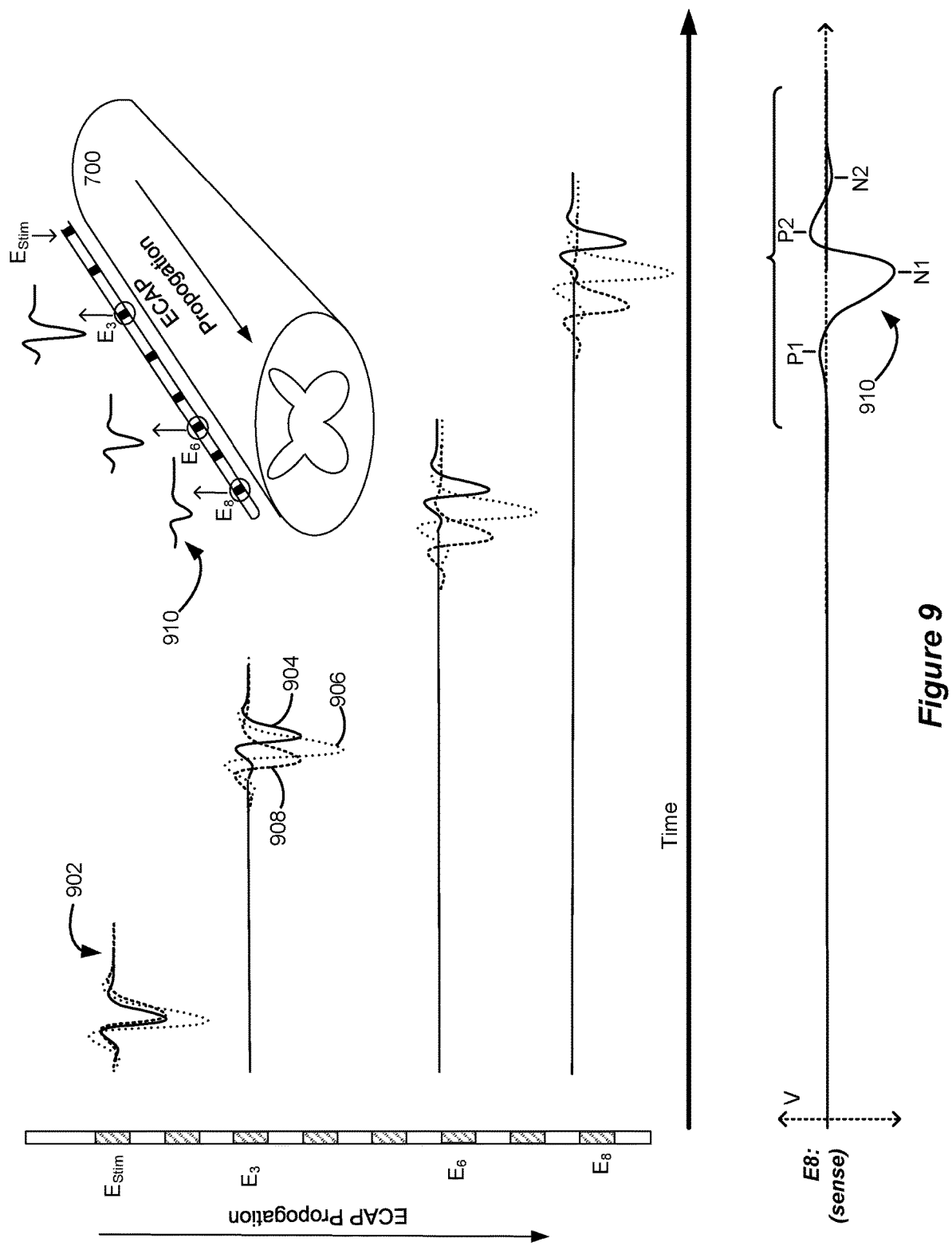
FIG. 9 shows propagation of ECAP components.

For clarity, three populations of neural elements are illustrated in FIG. 9. A person of skill in the art will appreciate that, in practice, there may be a greater number of therapeutically relevant populations of neural elements for a given therapy and for a given patient's anatomy. Each of the populations may have different propagation velocities that contribute to the shape of a sensed ECAP. Some of the component populations may be associated with a therapeutic effect while others of the component populations may be associated with a side effect, for example. Aspects of the disclosure relate to resolving sensed ECAPs into contributions of its component action potentials so that the effect of stimulation on the components can be understood. The effect of stimulation on the component action potentials can be used to guide and optimize stimulation in an open loop and/or closed loop system. In other words, the component action potential (resolved from the ECAP) is used as a biomarker for optimizing therapy or minimizing side effects.

Sensed ECAPs have been used to guide and optimize stimulation. For example, U.S. Patent Publication No. 2017/

0296823 (referred to herein as the '823 Application), published Oct. 19, 2017, describes a pulse generator system configured to determine one or more ECAP shape parameters and, based on those parameters, adjust the stimulation program to promote desynchronous firing of neural elements. The contents of the '823 Application are incorporated herein by reference. In view of the above discussion, it should be apparent to the reader that sensed ECAP signals described in the '823 Application are a summation of contributions of multiple populations of neural elements, which combine to produce the sensed ECAP signals. An object of the present disclosure is to decompose such summed ECAP signals into the component populations and determine the effects of stimulation on those component populations.

Figure 10:
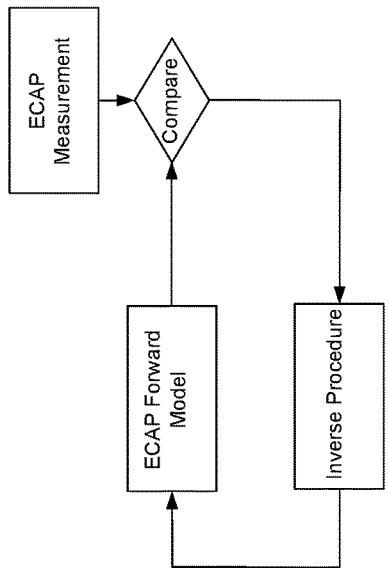
FIG. 10 shows an overview of a method for decomposing measured ECAPs into components.

FIG. 10 illustrates an overview of embodiments of the disclosed methods and systems. As explained in greater detail below, a forward model is constructed based on a number of baseline source modeled neural elements with weights associated with each modeled neural element. An ECAP forward model is used to model a neural response (e.g., an ECAP) at measurement site, wherein the modeled neural response signal is a summation of contributions from the baseline modeled neural elements (and their respective weights). The modeled neural response is compared to a measured neural response to refine the baseline source model using the inverse procedure. Generally, the modeled neural response may be any electrical change of the modeled neural elements caused by a stimulus, for example, a transmembrane current or a voltage induced by a transmembrane potential. An example of a modeled neural response is a modeled ECAP.

Figure 11:
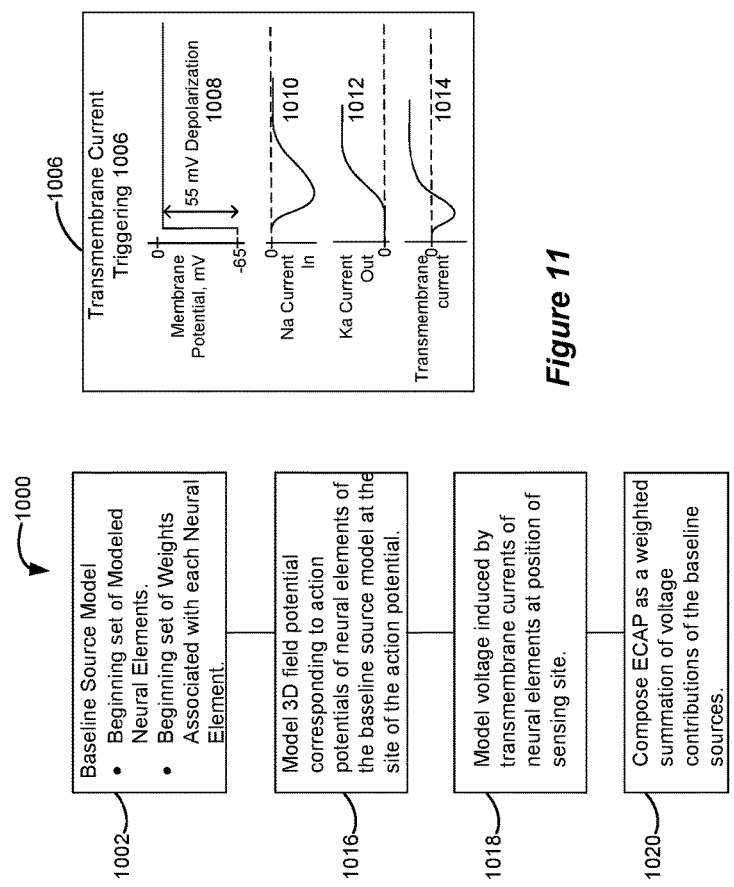
FIG. 11 shows a forward model for composing an ECAP from component neural elements.

FIG. 11 provides an overview of a forward model 1000 for modeling an ECAP as a weighted summation of potential components of a distribution of component modeled neural elements. The forward model uses a baseline source model 1002 comprising a beginning set of modeled neural elements (or neural populations). A weight is associated with each neural element or neural population. For example, the baseline source model may include three neural elements— small, medium, and large—as described above with reference to FIG. 9. Alternatively, a beginning set of modeled neural elements and/or their associated weights may be determined based on analysis of pre-processed ECAP measurements. According to this embodiment, a pre-processed ECAP measurement is statistically analyzed to predict how many neural elements contributed to the ECAP signal and to assign a weight to each of the component neural elements. Examples of such analysis includes principal component analysis (PCA) and independent component analysis (ICA).

Action potentials (see FIG. 6) of each neural element of the baseline source model are associated with a transmembrane current for each neural element. The sequence of events triggering the transmembrane current is illustrated in inset 1006 of FIG. 11. When the neural element experiences a transmembrane potential change exceeding a threshold value of about −55 mV, that causes the membrane of the neural element to depolarize 1008. When the membrane depolarizes, sodium ions in the extracellular environment move across the membrane into the neural element 1010 and potassium ions exit the neural element 1012 across the membrane into the extracellular environment. The combined movement of sodium and potassium ions across the neural membrane results in a transmembrane current 1014. The transmembrane current 1010 can be thought of as providing a current source within the physiological environment of the neural element.

Figure 12:
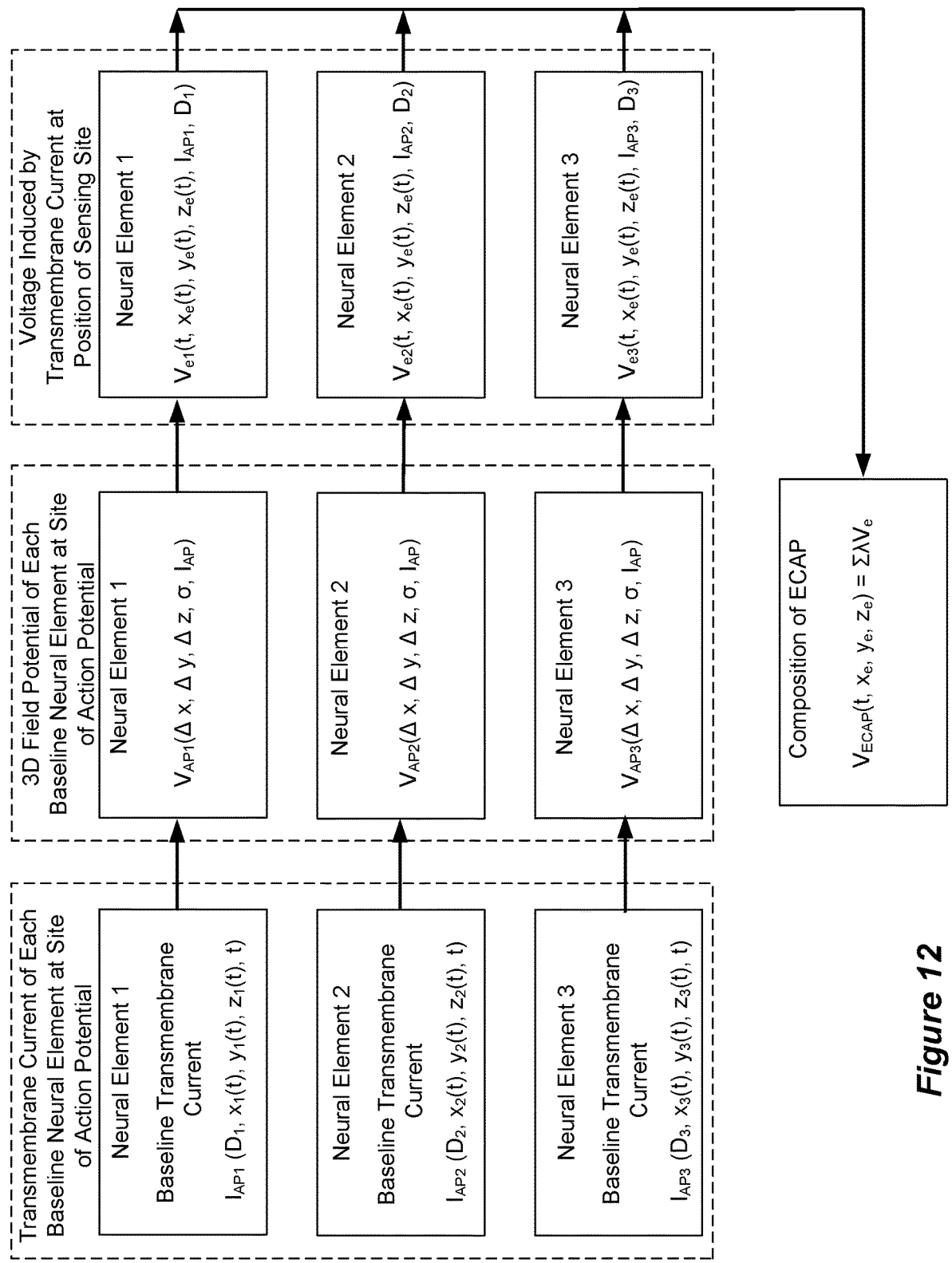
FIG. 12 shows an application using a forward model to compose an ECAP from three component neural elements.

The baseline source model includes the transmembrane currents associated with each of the modeled neural elements. FIG. 12 illustrates an embodiment wherein the transmembrane current of three neural elements are modeled. For example, the neural elements may correspond to large, medium, and small fibers as in the above example. The transmembrane current $I_{AP_n}$ at the site of the action potential for each neural element is a function of the diameter of the neural element $D_n$ and location of the neural element ($x_n(t)$, $y_n(t)$, and $z_n(t)$), and time t. As the transmembrane current is a function of time, the transmembrane currents may be modeled as developing over time. Thus, the modeled transmembrane currents $I_{AP_n}$ at a specific site (($xn(t)$, $yn(t)$, and $zn(t)$) are referred to as a time series of transmembrane currents. The depolarization and hyperpolarization process is a dynamic process where the transmembrane potential changes over time and thus the voltage-sensitive ion channels have time-varying conductivity. Therefore, the current flow is a time-varying process as well. Examples of modeled transmembrane currents are known in the art. For example, see Kandel et al., Principles of Neural Science, 4$^{th}$ edition, Part II Cell and Molecular Biology of the Neuron, 2000. In addition, since the action potentials propagates along the neural axons, the transmembrane current source is also a function of site (($xn(t)$, $yn(t)$, and $zn(t)$) over time.

It should be noted that the baseline source model may be a model or a mathematical approximation. The model can be a simplified or reduced model such as linear/passive model or more complicated model such as non-linear/active model of neurons, which incorporate parameters such as the geometrical (e.g. diameter, length, size or neural structure et al), physiological (e.g. myelinated or unmyelinated fibers, resting potentials, time constant or gate probability of ion channels, et al) and electrical properties (e.g. conductivity/resistivity, capacitance, et al) of the neural elements. Baseline sources, and refinements thereof, based on any of these methods are included in the term "modeled neural elements" in this disclosure.

The transmembrane current of each of the neural elements induces a field potential within the extracellular environment of the populations of the neural elements. Referring again to FIG. 11, the forward model 1000 includes modeling the 3D field potential induced by the transmembrane currents of the neural elements of the baseline source model in an extracellular volume surrounding the site of the action potential 1016. Referring to FIG. 12, the field potential $V_{AP}$ within a volume of each of the neural elements surrounding the site of the action potential is a function of the volume (i.e., the distance $\Delta x$, $\Delta y$, $\Delta z$ from the neural element), the conductivity $\sigma$ of the medium, and the size of the transmembrane current $I_{AP_n}$ for the neural element. The conductivity is modeled based on known physiological conductivities, which may also vary by spatial dimension (i.e. $\sigma_x$, $\sigma_y$, $\sigma_z$). The 3D field can be modeled using simple numerical model, such as point source model, more complex numerical methods, such as finite element analysis (FEM), or analytical fittings to complex numerical solution. Examples of FEM modeling of the structure and electric properties are provided in Lee, et al., *Predicted effects of pulse width programming in spinal cord stimulation: a mathematical modeling study*, Med. Biol. Eng. Comput., (2011) 49:765-774, the contents of which are incorporated herein by reference. Examples of analytical fitting are described in U.S. Pat. No. 8,233,992 and the references cited therein. U.S. Pat. No. 8,233,992, issued Jul. 31, 2012 is incorporated herein by reference in its entirety.

Referring again to FIG. 11, the forward model 1000 computes a voltage induced by the transmembrane current at a sensing site that is a distance away from the site of the action potential 1018. Referring to FIG. 12, for each of the neural elements, the induced voltage at the sensing electrode $V_e$ is a function of the position of the recording electrode ($x_e(t)$, $y_e(t)$, $z_e(t)$), time t, the transmembrane current $I_{AP}$ from the neural element of diameter D. The sensed voltage is computed by calculating the distance between the sites of recording electrodes and the sites of transmembrane current source $\Delta x$, $\Delta y$, $\Delta z$ and input to the model 1016.

Referring to FIG. 11, the modeled ECAP at the recording site can be composed as a weighted summation of the voltages induced from each of the baseline neural elements. In other words, the modeled ECAP ($V_{ECAP}$) is a function of time t and position of the sensing electrode (xe, ye, ze) and is equal to the sum of the voltage contributions of the component baseline neural elements, each multiplied by a weighting factor $\lambda$. The result of the forward model is, thus, a modeled ECAP at a position of a sensing (xe, ye, ze). In should be noted that multiple sensing cites (multiple channels) can be modeled and recorded.

Figure 13:
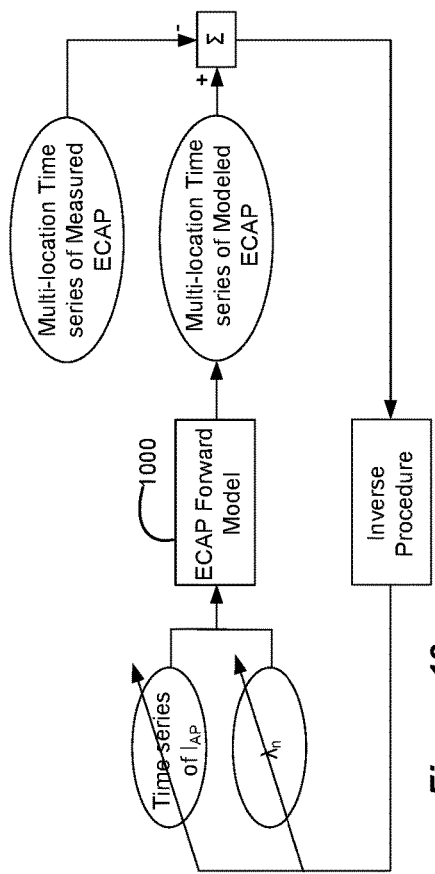
FIG. 13 shows an algorithm for refining an ECAP model and identifying neural components.

FIG. 13 illustrates how the forward model 1000 is refined based on measured ECAPs. A time series of transmembrane currents $I_{AP}$ and weights $\lambda_n$ associated with a baseline source model (as described above) comprising n neural elements is provided to the forward model 1000. As described above, the forward model 1000 estimates a modeled ECAP as a linear combination of voltages induced at a sensing site derived from the time series of transmembrane currents.

According to the embodiment illustrated in FIG. 13, the forward ECAP model estimates the ECAP multiple locations, i.e., at multiple sensing sites corresponding to multiple sensing electrodes. The forward model is also a time series model, in that it models how the ECAP develops at each sensing site as a function of time. By modeling the ECAP at multiple locations and at multiple times, the model can estimate ECAP shapes featuring contributions of the component neural elements of the baseline source model having different propagation rates (and, thus, different sizes). As explained above with reference to FIG. 9, at the earliest time the ECAP shape is dominated by electrical activity within the larger fibers. As time progresses, the smaller fibers influence the shape of the ECAP signal. Likewise, at a given time, activity of a larger fiber may be present at a more distant sensing site while electrical activity at a nearer sensing site is dominated by contributions from smaller fibers.

Referring again to FIG. 13, the multi-location time series of modeled ECAPs is compared to multi-location time series of measured ECAPs. Differences in the modeled and measured ECAPs indicate an unoptimized model of the time series of transmembrane currents $I_{AP}$ and/or unoptimized selection of weights $\lambda_n$ of the neural elements of the underlying baseline source model to represent the result of the actual physiological system under the conditions of the measurements. The model of transmembrane currents $I_{AP}$ and/or weights $\lambda_n$ of the baseline source model can be optimized by solving an inverse problem of the ECAP model, i.e. find the best $I_{AP}$ and/or $\lambda_n$ such that the modeled ECAP best approximates the measured ECAP, or in other words, the difference between the modeled and measured ECAP is minimized. This inverse problem may be formulated in different mathematical ways and solved using various optimization algorithm and methods, such as linear programming method, least squares minimization, greatest gradient method, etc.

Figure 14:
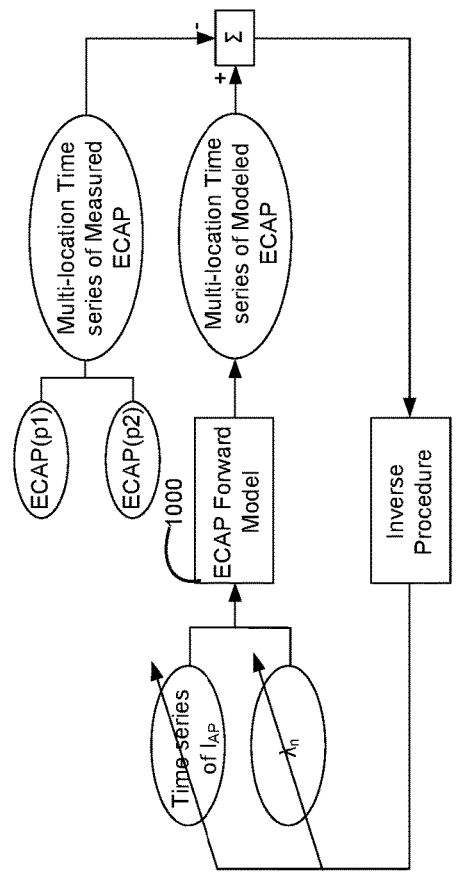
FIG. 14 an algorithm for refining an ECAP model and identifying neural components.

FIG. 14 illustrates an embodiment wherein measured ECAPs resulting from different stimulation parameters are used to refine the baseline source model and identify neural components. A time series of transmembrane currents $I_{AP}$ and weights $\lambda_n$ associated with a baseline source model (as described above) comprising n neural elements is provided to the forward model 1000. The resulting multi-location time series of modeled ECAPs are compared with a multi-location time series of measured ECAPs resulting ECAP(p1) from a first set of stimulation parameters. The inverse of the forward model procedure can be used adjust the transmembrane currents $I_{AP}$ and/or weights $\lambda_n$ of the baseline source model, as described above. The multi-location time series of modeled ECAPs resulting from the updated baseline source model can then be compared to a second multi-location time series of measured ECAPs resulting ECAP(p2) from a second set of stimulation parameters. Difference between the modeled (under parameter set 1) and measured (under parameter set 2) ECAP shapes indicate a difference in neural recruitment resulting from the two sets of stimulation parameters.

According to some embodiments, stimulation parameters can be titrated and the neural components of the baseline source model can be incrementally adjusted. Assume that the response of a given neural population remains constant beyond a threshold stimulation. Once the threshold stimulation is reached, then additional contributions to a measured ECAP can be assumed to indicate an additional neural component. Such incrementally extracted neural components can be used to update the baseline source model.

It should be noted that noise contained within the measured ECAP signals can complicate correlating the measured and modeled ECAPs. Thus, some embodiments described herein include preprocessing of the measured ECAP signals to extract or refine the ECAPs with respect to signal noise. Examples of such signal preprocessing include band pass filtering, signal averaging, and the like. One suitable method of extracting a measured ECAP within a noisy is described in co-owned U.S. Pat. No. 10,926,092, the contents of which are incorporated by reference. Moreover, tolerance for noise may be built into the model.

As explained above, the methods described with reference to FIGS. 11-14 identify the component neural elements that contribute to measured ECAP signals. That identification is based on a model that incorporates modeled biological features of the neural components, i.e., modeled neural elements (or neural populations). The modeled potential fields also incorporate modeled body tissue as the volume through which the potential fields are conducted. With the ability to decompose sensed ECAP measurements into contributions of the component neural elements, a clinician can then optimize therapy using one or more of the component neural elements as a biomarker.

Figure 2:
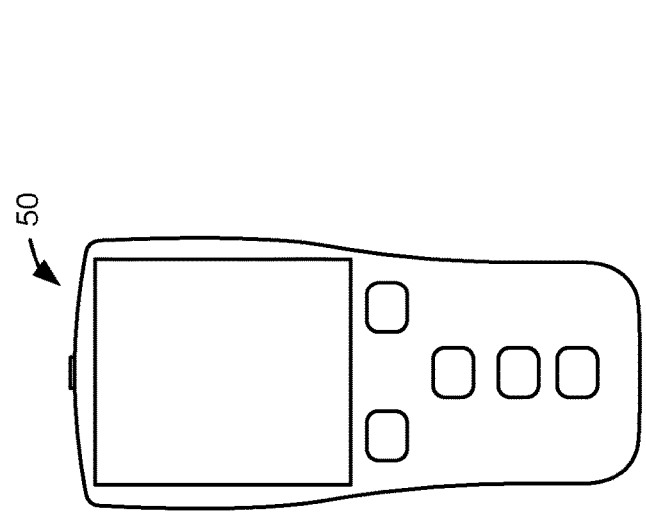
FIG. 2 shows a hand-held external controller for communicating with an IPG.

When a patient is implanted with an IPG, it is important to determine a stimulation program that will best alleviate a patient's symptoms. Part of this "fitting" process includes determining which electrodes should be activated by the IPG 100 (or the ETS 170); the polarity of these active electrodes; the amplitude of stimulation; (if stimulation is issued in pulses) the pulse width, frequency, the duty cycle (DC), and shape of the waveform (e.g., pulses); etc. Initial fitting of a patient to determine a stimulation program that is effective usually occurs using a clinician programmer 90 (FIG. 3), but fitting or stimulation program adjustment can also occur using a patient external controller 50 (FIG. 2). Fitting can occur both during an external trial phase as described earlier and after a permanent IPG 100 has been implanted.

Figure 15:
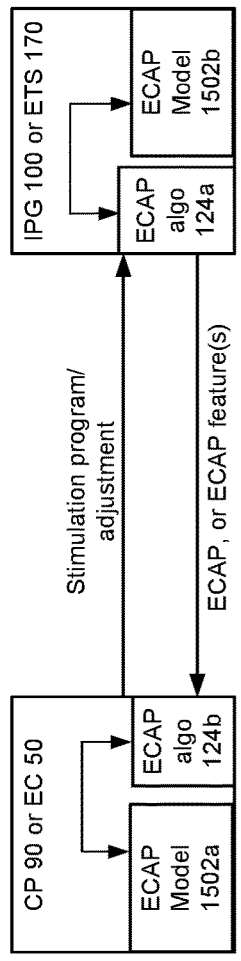
FIG. 15 shows a system embodying an ECAP algorithm.

Aspects of the disclosed methods for decomposing measured ECAPs to optimize therapy can be performed during the initial (or subsequent) fitting procedures. As mentioned above, the IPG 100 (or ETS 170) includes control circuitry 102 into which an ECAP algorithm 124a can be programmed. As also noted above, the ECAP algorithm can alternatively operate with the assistance of external devices, as shown in FIG. 15, which shows an external programming device (such as the clinician programmer 90 or external controller 50) in wireless communication with the IPG 100 (or ETS 170). In this example, an ECAP algorithm 124b is included in the external device, which can receive information from the IPG 100 (or ETS 170) regarding the ECAPs it measures, process the ECAP, and send a stimulation program (or adjustment) to the IPG. ECAP algorithm 124a again operates in the IPG 100 (or ETS 170), but, in this example, off-loads ECAP analysis and stimulation program adjustment to ECAP algorithm 124b in the external device. A system as shown in FIG. 15 is particularly useful when fitting the implant patient, i.e., when determining a stimulation program that would be useful in treating the patient's symptoms. The embodiment of the clinician programmer 90 (or external controller 50) illustrated in FIG. 15 also includes an ECAP model 1502a, which includes programming for modeling ECAPs, as described above. For example, the ECAP model 1502a may include one or more baseline source models (modeled neural elements and associated weights) as well as parameters set for physiological properties, such as tissue conductivity, etc. It should be noted here, that various selectable parameter sets and/or templates may be used with the ECAP model. The baseline source models and parameter sets may be comprised within a library, for example. For example, there may be parameter sets based on patient profiles, which consider the patient's sex, weight, body fat composition, age, etc. Additionally, the parameter sets or templates may be based on the particular neural anatomy implicated by the therapy, for example, spinal anatomy, brain anatomy, vagus nerve anatomy, sacral nerve anatomy, and the like. The baseline source models and associated parameter sets/templates may be updated based on research and/or based on empirical determinations. As illustrated in FIG. 15, the ECAP 1502b model can transmit data to/from the ECAP algorithm 124b.

As also illustrated in FIG. 15, some or all the ECAP model 1502b may be configured within the IPG 100 (or ETS 170). Depending on the computational intensity of the operations, the complexity of the neural modeling, etc., some or all the operations described above may be executed within the IPG 100. Alternatively, some operations may be executed in the external device and others in the IPG. In embodiments of closed loop control of therapy, for example, the external device may be used during the fitting process to "train" the IPG 100 to detect recruitment of certain neural elements or to detect features of ECAP signals indicative of such neural recruitment and to adjust the stimulation accordingly.

One skilled in the art will understand that the ECAP algorithm 124a and 124b, the ECAP model 1502a/1502b, and/or any supporting user interface program will comprise instructions that can be stored on non-transitory machine-readable media, such as magnetic, optical, or solid-state memories. Such memories may be within the IPG or ETS itself (i.e., stored in association with control circuitry 102), within the external system, or readable by the external system (e.g., memory sticks or disks). Such memories may also include those within Internet or other network servers, such as an implantable medical device manufacturer's server or an app store server, which may be downloaded to the external system. The stored instructions for ECAP algorithm and ECAP model are executed using one or more processors (or microprocessors) as known to one of skill in the art.

Figure 16:
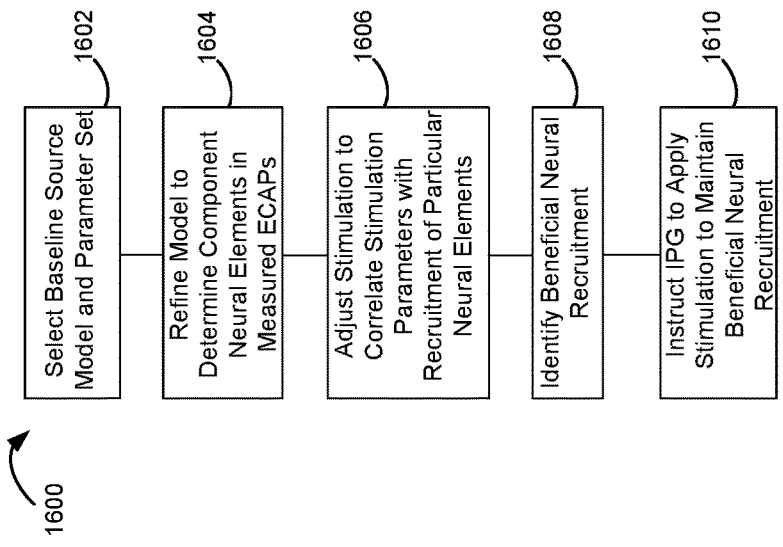
FIG. 16 shows a workflow for using a decomposition of a ECAP to maintain beneficial neural recruitment.

FIG. 16 illustrates a method 1600 of using the decomposition of ECAPs to optimize stimulation. According to the illustrated embodiment, the method 1600 is performed during the fitting process. First, an appropriate baseline source model and parameter set is selected 1602. As described above, the initial baseline source model may be selectable based on characteristics of the patient and/or the desired therapy. The baseline source model is then refined 1604, as described earlier, by comparing modeled ECAPs generated using the baseline source model to measured ECAPS. As a result, the model determines the component neural elements comprising the measured ECAPs.

Having resolved the ECAPs into component neural elements, stimulation parameters can be adjusted (titrated) to correlate the stimulation parameters with recruitment of particular neural elements 1606. For example, it may be found that one set of stimulation parameters preferentially stimulates smaller neural elements while a different set of stimulation parameters preferentially stimulates larger neural elements. It should be noted that any set or subset of stimulation parameters may be adjusted and correlated to neural recruitment. For example, amplitude, pulse width, pulse rate, pulse shape, stimulation electrode, etc., may be adjusted to determine how the adjustment correlates to neural recruitment. For example, it may be found that complex pulse shapes, including pre-pulsing may selectively excite or inhibit activation of certain neural elements.

Having identified how to selectively recruit the component neural elements comprising measured ECAPs, particular neural elements can be correlated to a therapeutic effect to the patient 1608. For example, it may be found that selectively recruiting one neural element (or population of neural elements) results in pain relief, whereas inhibiting a different neural element (or population) alleviates a side effect. Correlation of neural recruitment may be informed by patient providing feedback relating to their level of pain, relief, side effect, paresthesia, etc., and may also be informed by patient physiological response, such as heart rate, temperature, blood pressure, etc.

Once the desired neural recruitment is established based on the ECAP model, the IPG can be instructed to apply stimulation directed at maintaining the selected neural recruitment 1610. For example, the IPG can be instructed to adjust the stimulation if the selected neural recruitment varies from the established set point. Thus, embodiments of the disclosed methods provide closed-loop feedback for maintaining neuromodulation.

Although particular embodiments have been shown and described, the above discussion should not limit the present invention to these embodiments. Various changes and modifications may be made without departing from the spirit and scope of the present invention. Thus, the present invention is intended to cover equivalent embodiments that may fall within the scope of the present invention as defined by the claims.

What is claimed is:

1. A method for adjusting electrical stimulation provided to a patient's neural tissue using an implantable electrode lead comprising a plurality of electrodes, wherein the patient's neural tissue comprises a plurality of neural populations, the method comprising:
  using a first one or more of the electrodes to issue electrical stimulation to the patient's neural tissue, using a second one or more of the electrodes to record electrical signals in the patient's neural tissue, wherein the electrical signals comprise action potentials evoked by neural populations recruited by the stimulation, decomposing the recorded electrical signals to determine contributions of one or more of the recruited neural populations to the recorded electrical signals by comparing the recorded electrical signals to modeled neural responses derived from a model, wherein the model comprises:

a plurality of modeled neural elements and a weight associated with each of the modeled neural populations, and wherein the modeled neural responses comprise a weighted summation of modeled action potentials evoked in the modeled neural populations by the stimulation waveform, and using the determined contributions to adjust the stimulation.

2. The method of claim 1, wherein the plurality of neural populations comprises neural populations having different fiber sizes.

3. The method of claim 1, wherein adjusting the stimulation waveform comprises adjusting one or more of an amplitude, pulse width, or pulse rate of the electrical stimulation.

4. The method of claim 1, wherein decomposing the recorded electrical signals to determine contributions of one or more of the recruited neural populations further comprises:

refining the model based on the comparison to minimize a difference between the modeled neural responses and the recorded electrical signals, and using the refined model to determine contributions of one or more of the populations of neural elements.

5. The method of claim 4, wherein refining the model comprises adjusting the weights associated with one or more of the neural populations.

6. The method of claim 4, wherein the model comprises modeled transmembrane currents associated with the modeled action potentials of each of the plurality of modeled neural populations.

7. The method of claim 6, wherein modeling compound action potentials arising from action potentials of one or more of the modeled neural populations comprises modeling voltages induced by the modeled transmembrane currents.

8. The method of claim 7, wherein the modeled compound action potentials comprise a weighted summation of the modeled voltages induced by the modeled transmembrane currents.

9. A device for providing electrical stimulation to a patient using an electrode lead implanted in the patient, wherein the electrode lead comprises a plurality of electrodes, the device comprising:

a microprocessor programmed to:

cause a first one or more of the electrodes to issue electrical stimulation to the patient's neural tissue, cause a second one or more of the electrodes to record electrical signals in the patient's neural tissue, wherein the electrical signals comprise action potentials evoked by neural populations recruited by the stimulation, decompose the recorded electrical signals to determine contributions of one or more of the recruited neural populations to the recorded electrical signals by comparing the recorded electrical signals to modeled neural responses derived from a model, wherein the model comprises:

a plurality of modeled neural elements and a weight associated with each of the modeled neural populations, and wherein the modeled neural responses comprise a weighted summation of modeled action potentials evoked in the modeled neural populations by the stimulation waveform, and use the determined contributions to adjust the stimulation.

10. The device of claim 9, wherein adjusting the stimulation waveform comprises adjusting one or more of an amplitude, pulse width, or pulse rate of the electrical stimulation.

11. The device of claim 9, wherein decomposing the recorded electrical signals to determine contributions of one or more of the recruited neural populations further comprises:

refining the model based on the comparison to minimize a difference between the modeled neural responses and the recorded electrical signals, and using the refined model to determine contributions of one or more of the populations of neural elements.

12. The device of claim 11, wherein wherein refining the model comprises adjusting the weights associated with one or more of the neural populations.

13. The device of claim 11, wherein the model comprises modeled transmembrane currents associated with the modeled action potentials of each of the plurality of modeled neural populations.

14. The device of claim 13, wherein modeling compound action potentials arising from action potentials of one or more of the modeled neural populations comprises modeling voltages induced by the modeled transmembrane currents.

15. The device of claim 14, wherein the modeled compound action potentials comprise a weighted summation of the modeled voltages induced by the modeled transmembrane currents.

* * * * *